(12) United States Patent
Petrotchenko et al.

(10) Patent No.: US 8,691,515 B2
(45) Date of Patent: Apr. 8, 2014

(54) METHODS FOR EARLY DETECTION OF BLOOD DISORDERS

(75) Inventors: Evgeniy V. Petrotchenko, Victoria (CA); Christoph Borchers, Victoria (CA)

(73) Assignee: UVic Industry Partnerships Inc., Victoria, BC (CA)

( * ) Notice: Subject to any disclaimer, the term of this patent is extended or adjusted under 35 U.S.C. 154(b) by 0 days.

(21) Appl. No.: 13/378,844

(22) PCT Filed: Jul. 7, 2010

(86) PCT No.: PCT/CA2010/001023
§ 371 (c)(1),
(2), (4) Date: Jan. 13, 2012

(87) PCT Pub. No.: WO2011/003182
PCT Pub. Date: Jan. 13, 2011

(65) Prior Publication Data
US 2012/0107859 A1    May 3, 2012

Related U.S. Application Data

(60) Provisional application No. 61/223,573, filed on Jul. 7, 2009.

(51) Int. Cl.
*C12P 21/06*    (2006.01)

(52) U.S. Cl.
USPC .......................... 435/7.25; 435/23; 435/68.1

(58) Field of Classification Search
None
See application file for complete search history.

(56) References Cited

PUBLICATIONS

Sinz, "Chemical cross-linking and mass spectrometry for mapping three-dimensional structures of proteins and protein complexes." (2003) Journal of Mass Spectrometry, 38: 1225-1237.*

Yamazaki et al. "Studies on Reactions of the N-Phophonium Salts of Pyridines." (1974) Journal of Polymer Science, vol. 12: 2149-2154.*
Biroccio et al., "A Quantitative Method for the Analysis of Glycated and Glutathionylated Hemoglobin by Matrix-Assisted Laser Desorption Ionization-Time of Flight Mass Spectrometry," *Anal. Biochem.* 336:279-288, 2005.
Kalkhof and Sinz, "Chances and Pitfalls of Chemical Cross-Linking with Amine-Reactive N-hydroxysuccimide Esters," *Anal. Bioanal. Chem.* 392:305-312, 2008.
Leavell et al., "Strategy for Selective Chemical Cross-Linking of Tyrosine and Lysine Residues," *Am. Soc. Mass. Spectrom.* 15:1604-1611, 2004.
Mädler et al., "Chemical Cross-Linking with NHS Esters: A Systematic Study on Amino Acid Reactivities," *J. Mass. Spectrom.* 44:694-706, 2009.
Zurbriggen, et al., "Analysis of Minor Hemoglobins by Matrix-Assisted Laser Desorption/Ionization Time-of-Flight Mass Spectrometry," *Clin. Chem.* 51:989-996, 2005.
Brady et al., "Characterization of Nonenzymatic Glycation on a Monoclonal Antibody," *Anal. Chem.* 79:9403-9413, 2007.
Lee and Kim, "Immobilization of Aminophenylboronic Acid on Magnetic Beads for the Direct Determination of Glycoproteins by Matrix Assisted Laser Desorption Ionization Mass Spectrometry," *J. Am. Soc. Mass Spectrom.* 16:1456-1460, 2005.

* cited by examiner

*Primary Examiner* — Jon P Weber
*Assistant Examiner* — Teresa E Knight
(74) *Attorney, Agent, or Firm* — Klarquist Sparkman, LLP

(57) ABSTRACT

Disclosed herein are methods of detecting blood disorders, such as diabetes. In particular examples the method includes contacting a blood sample with an amine reagent, blocking an excess of the amine reagent with a blocking reagent, digesting the modified blood sample with trypsin to produce a digested blood sample containing a plurality of glycated N-terminal peptides and non-glycated N-terminal peptides, then analyzing the digested blood sample with MALDI MS. Also provided are reagents for use in such methods.

17 Claims, 13 Drawing Sheets

3161 + 105 + 105 + 105 = 3476

3161 + 162 + 105 + 105 = 3533

SEQUENCE LISTING

```
<160> NUMBER OF SEQ ID NOS: 10

<210> SEQ ID NO 1
<211> LENGTH: 30
<212> TYPE: PRT
<213> ORGANISM: Homo sapiens

<400> SEQUENCE: 1

Val His Leu Thr Pro Val Glu Lys Ser Ala Val Thr Ala Leu Trp Gly
1               5                   10                  15

Lys Val Asn Val Asp Glu Val Gly Gly Glu Ala Leu Gly Arg
            20                  25                  30

<210> SEQ ID NO 2
<211> LENGTH: 8
<212> TYPE: PRT
<213> ORGANISM: Homo sapiens

<400> SEQUENCE: 2

Val His Leu Thr Pro Lys Glu Lys
1               5
```

```
<210> SEQ ID NO 3
<211> LENGTH: 8
<212> TYPE: PRT
<213> ORGANISM: Homo sapiens

<400> SEQUENCE: 3

Val His Leu Thr Pro Glu Glu Lys
1               5

<210> SEQ ID NO 4
<211> LENGTH: 30
<212> TYPE: PRT
<213> ORGANISM: Homo sapiens

<400> SEQUENCE: 4

Val His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg
            20                  25                  30

<210> SEQ ID NO 5
<211> LENGTH: 30
<212> TYPE: PRT
<213> ORGANISM: Homo sapiens

<400> SEQUENCE: 5

Val His Leu Thr Pro Lys Glu Lys Ser Ala Val Thr Ala Leu Trp Gly
1               5                   10                  15

Lys Val Asn Val Asp Glu Val Gly Gly Glu Ala Leu Gly Arg
            20                  25                  30

<210> SEQ ID NO 6
<211> LENGTH: 8
<212> TYPE: PRT
<213> ORGANISM: Homo sapiens

<400> SEQUENCE: 6

Val His Leu Thr Pro Val Glu Lys
1               5

<210> SEQ ID NO 7
<211> LENGTH: 10
<212> TYPE: PRT
<213> ORGANISM: Artificial Sequence
<220> FEATURE:
<223> OTHER INFORMATION: N-terminal peptide of albumin modified at
      N-terminal and Lys residues following treatment with amine
      reactive reagent.
<220> FEATURE:
<221> NAME/KEY: MISC_FEATURE
<222> LOCATION: (1)..(1)
<223> OTHER INFORMATION: N terminal amino acid modified following
      reaction with an amine reactive reagent
<220> FEATURE:
<221> NAME/KEY: MISC_FEATURE
<222> LOCATION: (4)..(4)
<223> OTHER INFORMATION: Lys modified following reaction with an amine
      reactive reagent

<400> SEQUENCE: 7

Asp Ala His Lys Ser Glu Val Ala His Arg
1               5                   10

<210> SEQ ID NO 8
<211> LENGTH: 31
<212> TYPE: PRT
<213> ORGANISM: Artificial Sequence
```

```
<220> FEATURE:
<223> OTHER INFORMATION: N-terminal peptide of alpha chain of hemoglobin
      modified at N-terminal and Lys residues following treatment with
      amine reactive reagent.
<220> FEATURE:
<221> NAME/KEY: MISC_FEATURE
<222> LOCATION: (1)..(1)
<223> OTHER INFORMATION: N terminal amino acid modified following
      reaction with an amine reactive reagent
<220> FEATURE:
<221> NAME/KEY: MISC_FEATURE
<222> LOCATION: (7)..(7)
<223> OTHER INFORMATION: Lys modified following reaction with an amine
      reactive reagent
<220> FEATURE:
<221> NAME/KEY: MISC_FEATURE
<222> LOCATION: (11)..(11)
<223> OTHER INFORMATION: Lys modified following reaction with an amine
      reactive reagent

<400> SEQUENCE: 8

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: N-terminal peptide of beta chain of free
      hemoglobin modified at N-terminal and Lys residues following
      treatment with amine reactive reagent.
<220> FEATURE:
<221> NAME/KEY: MISC_FEATURE
<222> LOCATION: (8)..(8)
<223> OTHER INFORMATION: Lys modified following reaction with amine
      reactive agent.
<220> FEATURE:
<221> NAME/KEY: MISC_FEATURE
<222> LOCATION: (17)..(17)
<223> OTHER INFORMATION: Lys modified following reaction with amine
      reactive agent.

<400> SEQUENCE: 9

Val His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: N-terminal peptide of beta chain of glycated
      hemoglobin modified at Lys residues following treatment with amine
      reactive reagent.
<220> FEATURE:
<221> NAME/KEY: MISC_FEATURE
<222> LOCATION: (1)..(1)
<223> OTHER INFORMATION: N terminal Val is glycated
<220> FEATURE:
<221> NAME/KEY: MISC_FEATURE
<222> LOCATION: (8)..(8)
<223> OTHER INFORMATION: Lys modified following reaction with amine
      reactive agent.
<220> FEATURE:
<221> NAME/KEY: MISC_FEATURE
<222> LOCATION: (17)..(17)
<223> OTHER INFORMATION: Lys modified following reaction with amine
      reactive agent.
```

```
<400> SEQUENCE: 10

Val His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg
            20                  25                  30
```

METHODS FOR EARLY DETECTION OF BLOOD DISORDERS

CROSS REFERENCE TO RELATED APPLICATIONS

This is the U.S. National Stage of International Application No. PCT/CA2010/001023, filed Jul. 7, 2010, which was published in English under PCT Article 21(2), which in turn claims priority to and the benefit of U.S. Provisional Application No. 61/223,573 filed on Jul. 7, 2009, which is incorporated herein in its entirety.

FIELD

This disclosure relates to diagnostic screening and monitoring assays. More particularly, this disclosure relates to diagnostic screening and monitoring assays for detecting blood disorders.

BACKGROUND

Hemoglobin is the iron-containing oxygen-transport metalloprotein in the red blood cells of vertebrates, and the tissues of some invertebrates. The chemical formulae of hemoglobin vary widely across species, and even slightly among subgroups of humans. In adult humans, the most common hemoglobin type is a tetramer called hemoglobin A. Hemoglobin A consist of non-covalently bound $\alpha$ and $\beta$ subunits. Mutations in the genes for the hemoglobin protein in a species result in hemoglobin variants. Hemoglobin variants are a part of the normal embryonic and fetal development, but mutant forms of hemoglobin in a population, may also be caused by variations in genetics. Some well-known genetic hemoglobin variants are responsible for diseases such as sickle-cell anemia. A separate class of diseases known as thalassemias are caused by underproduction of normal and abnormal hemoglobin and also, through problems with and mutations in globin gene regulation.

To a small extent, hemoglobin A slowly combines with glucose at the terminal valine of each $\beta$ chain and the resulting molecule is often referred to as HbAlc. As the concentration of glucose in the blood increases, the percentage of hemoglobin A that turns into HbAlc increases. In diabetics whose glucose usually runs high, the percent HbAlc also runs high. Long-term control of blood sugar concentration can be measured by the concentration of HbAlc. A higher glucose concentration results in more HbAlc. Because the reaction is slow, the HbAlc proportion represents glucose level in blood averaged over the half-life of red blood cells, is typically 50-55 days.

Diabetes mellitus commonly known as diabetes, is a group of metabolic diseases resulting in abnormally high blood sugar levels referred to as hyperglycemia. Blood glucose levels are controlled by a complex interaction of multiple chemicals and hormones in the body, including the hormone insulin. More specifically, Diabetes mellitus refers to a group of diseases that lead to high blood glucose levels due to defects in one of insulin secretion or insulin action. Type 1 diabetes is a consequence of a diminished production of insulin while Type II and gestational diabetes are resistant to the effects of insulin. Type II diabetes is the most prevalent form of diabetes. Type II diabetes is often asymptomatic in its early stages and can remain undiagnosed for many years. Diabetes and its treatments can cause many complications. Acute complications exemplified by hypoglycemia, ketoacidosis, or nonketoticii hyperosmolar coma, may occur if the disease is not adequately controlled. Serious long-term complications due to diabetes may include cardiovascular disease, chronic renal failure, retinal damage which can lead to blindness, several kinds of nerve damage, and micro-vascular damage, which may cause erectile dysfunction and poor wound healing. In the developed world, diabetes is the most significant cause of adult blindness in the non-elderly and the leading cause of non-traumatic amputation in adults.

There is often a long, latent, asymptomatic period during which people with Type II diabetes are undiagnosed. Most people are unaware they have Type II diabetes, but experience physiological complications from the disease. Many newly diagnosed Type II diabetes cases already show evidence of micro-vascular complications and serious effects and long term complications from the disease. Early detection of diabetes is essential and may help improve the outcome for people with Type II diabetes. Regular screening for diabetes will enhance quality and length of life for a diabetic person from reducing the severity and frequency of immediate effects or prevention and/or delay of long term complications.

Glycated substances are eliminated from the body slowly. Red blood cells, which have a consistent lifespan of 120 days, are easily accessible for measurement of recent increased presence of glycating product. This fact is used in monitoring blood sugar control in diabetes by monitoring the glycated hemoglobin level, also known as HbAlc. Measurements of HbAlc in the 4-6% range are considered normal, less than 7% is a well controlled diabetic, 7-8% is an average diabetic and greater than 8% is a poorly controlled diabetic. There are many known methods to screen for diabetes. The fast plasma glucose and oral glucose-tolerance tests are standard clinical tests. The fast plasma glucose test is measured in a blood sample taken after eight hours of complete fasting. The blood glucose tolerance test is measured in several blood samples taken at a series of intervals following the administration of a specific glucose load. A current screening method referred to as the plasma glucose test does not require fasting and includes a blood and/or urine test that measures plasma glucose levels with enzymatic assay. Another common screening method is to screen the blood for glycated hemoglobin (HbAlc) which is either based on charge difference between non-glycated and glycated hemoglobin using ion-exchange chromatography, electrophoresis, or isoelectric focusing or immunological methods employing antibodies against glycated N-terminal of $\beta$-chain of the hemoglobin. Recently, the first molecular assay for glycated hemoglobin was disclosed. The $\beta$-chain of hemoglobin was digested with Glu-C, providing an N-terminal hexapeptide which was measured using ElectroSpray Ionization Liquid Chromatography Mass Spectrometry (ESI-LC/MS). The current methods to screen and monitor for diabetes are expensive, laborious, and time-consuming, require highly skilled operators, unreliable, and often require repeat testing.

There are many types of known hemoglobin (Hb) molecules and many are associated with inherited blood disorders such as sickle cell, hemoglobin C, S—C, and E, thalassemia and analbuminaemia. The most common hemoglobin molecules are HbA, HbA2, HbF, HbS, HbC, Hgb H, and Hgb M. Healthy adults only have significant levels of HbA and HbA2. Some people may also have small amounts of HbF, which is the main type of hemoglobin in an unborn baby's body and certain diseases are associated with high HbF levels. HbS is an abnormal form of hemoglobin associated with sickle cell anemia. In adults, these hemoglobin molecules make up the following percentages of total hemoglobin. Hgb A1: 95% to 98%, Hgb A2: 2% to 3%, Hgb F: 0.8% to 2%, Hgb S: 0%, Hgb C: 0%. In infants and children, these hemoglobin molecules make up the following percentages of total hemoglobin, Hgb F (newborn): 50% to 80%, Hgb F (6 months): 8%, Hgb F (over 6 months): 1% to 2%. The presence of significant levels of abnormal hemoglobins may indicate hemoglobin C disease, rare hemoglobinopathy, sickle cell anemia, and thalassemia.

In general, people with these inherited blood disorders are physiologically vulnerable and are at higher risk of infection, stroke, heart failure, liver and acute chest syndrome. The current method to screen and monitor for blood disorders is the hemoglobin electrophoresis diagnostic test. This test is a widely used screening test and if the presence of the blood disorder is indicated, a second hemoglobin electrophoresis diagnostic test is preformed to confirm the first diagnosis. The current test that is used to screen and monitor for blood disorders is expensive, laborious, and time-consuming, require highly skilled operators, unreliable, and requires repeat testing.

BRIEF DESCRIPTION OF THE DRAWINGS

The present disclosure will be described in conjunction with reference to the following drawings in which.

SEQUENCE LISTING

SEQ ID NO: 1 is a mutant hemoglobin S peptide identified using the methods provided herein.

SEQ ID NOS: 2-3 are mutant and normal hemoglobin C peptide fragments, respectively.

SEQ ID NOS: 4-5 are normal and mutant hemoglobin C peptides, respectively.

SEQ ID NO: 6 is a mutant hemoglobin C peptide fragment.

SEQ ID NO: 7 is an N-terminal peptide for albumin modified at N-terminal and lysine residues following reaction with an amine reactive reagent.

SEQ ID NO: 8 is an N-terminal peptide for an α-chain of hemoglobin modified at N-terminal and lysine residues following reaction with an amine reactive reagent.

SEQ ID NO: 9 is an N-terminal peptide for an α-chain of hemoglobin modified at N-terminal and lysine residues following reaction with an amine reactive reagent.

DETAILED DESCRIPTION

The exemplary embodiments of the present disclosure relate to methods for screening and monitoring blood samples for detection of disorders.

As used herein, "MALDI MS" refers to Matrix-Assisted Laser Desorption/Ionization Mass Spectrometry*.

As used herein, "HbA1c" refers to glycated hemoglobin in a subject's blood;

As used herein, "N-terminal and/or N-terminus" refers to the end of a protein or polypeptide terminated by an amino acid with a free amine group;

As used herein, "Calibration Curve" refers to a plot showing an instrument's responses, i.e., analytical signal, with the concentration of the analyte (i.e., the substance to be measured). An operator prepares a series of standards across a range of concentrations approximate the anticipated concentration of analyte in subjects' samples. The concentrations of the standards must lie within the working range of the technique (i.e., instrumentation) being used. Analyzing each of these standards using the chosen technique will produce a series of measurements. For most analyses, a plot of instrument response vs. analyte concentration will show a linear relationship. An operator can assess the data generated from the samples and in reference to the calibration curve, perform an interpolation to determine the analyte concentrations in the samples.

Figure 1:
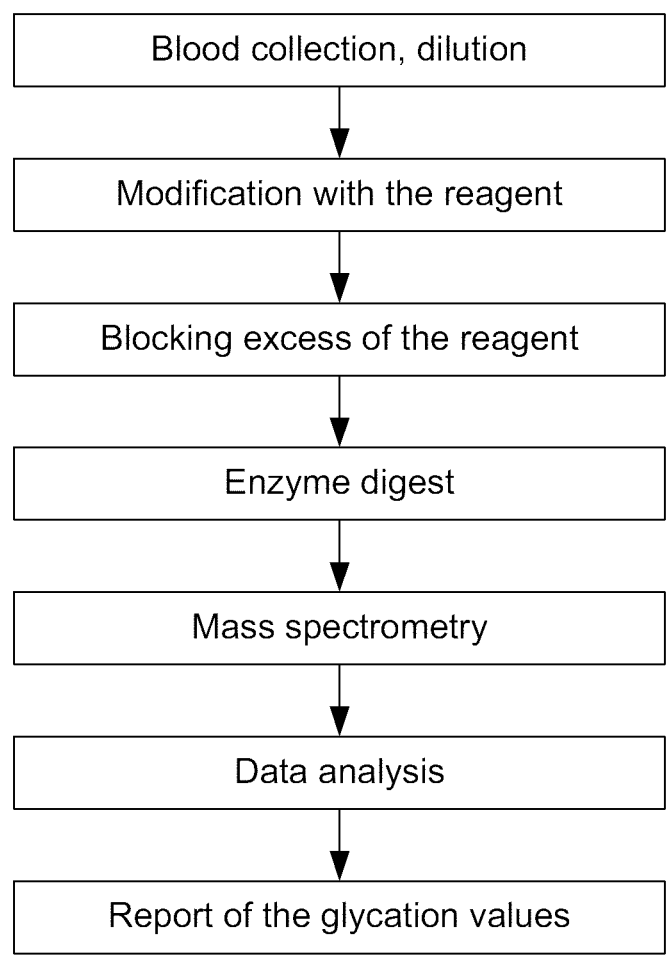
FIG. 1 is a schematic flowchart illustrating an exemplary method of the present disclosure.

The present disclosure relates to methods for screening and monitoring for Type I and Type II diabetes and blood disorders. An exemplary method for monitoring and screening for blood disorders according to one embodiment of the present disclosure is illustrated in FIG. 1. A subject's blood is collected in small quantities via blood spots and/or liquid blood samples, then diluted and modified with an amine reagent wherein the available amino groups of albumin or hemoglobin proteins are reacted with the amine reactive reagent thereby modifying the N-terminal and/or lysine side chains of the albumin and/or hemoglobin moieties. A blocking agent is then applied to the sample which is subsequently digested with an proteolytic enzyme. Suitable proteolytic enzymes that may be used when it is desirable to have proteolysis hindered by lysine groups modified by the amine agent, are exemplified by trypsin and Lys-C endoproteinase. Suitable proteolytic enzymes that may be used when it is desirable to have proteolysis unhindered by modified lysine groups, are exemplified by trypsin and Arg-C endoproteinase, Asp-N endoproteinase, pepsin, chymotrypsin, papain, and elastase. Ion signals corresponding to specific pairs of glycated and non-glycated N-terminal peptides are detected and measured using MALDI MS.

The disclosure described herein demonstrates that changes in glycation can be used to screen and monitor the population for Type I and Type II diabetes and other blood disorders.

Sample Preparation

It is known in the prior art that MALDI MS analyses can be conducted with biological fluids exemplified by blood, without pre-processing the biological fluid samples. Suitable biological fluids are exemplified by blood. One exemplary method of the present disclosure relates to processing a blood sample drawn from a subject. The blood sample may be diluted prior to processing. Alternatively, the blood sample may be placed onto a piece of paper and allowed to dry. The blood sample is then modified with an exemplary amine reagent wherein the amines preferentially bind to the alpha amino groups of N-terminals and/or epsilon amino groups of lysine side chains. The next step is application of a blocking reagent followed by digestion with an enzyme whereby the proteins are cleaved. Suitable proteolytic enzymes that may be used when it is desirable to have proteolysis hindered by lysine groups modified by the amine agent, are exemplified by trypsin and Lys-C endoproteinase. Suitable proteolytic enzymes that may be used when it is desirable to have proteolysis unhindered by modified lysine groups, are exemplified by trypsin and Arg-C endoproteinase, Asp-N endoproteinase, pepsin, chymotrypsin, papain, and elastase. The cleaved proteins, now referred to as peptides, are analysed with mass spectrometry wherein the ion signals corresponding to the specific pairs of glycated and non-glycated N-terminal peptides are measured.

Mass Spectrometric Analysis

The use of MALDI MS allows the extent of glycation to be rapidly obtained and further allows individual proteins of interest to be identified and quantified within a biological sample. The proteins of interest can be converted to peptides, and it is the peptides that are analyzed to give a corresponding ion signal. The matrix used during MALDI MS analysis can include many types of suitable organic molecules exemplified by α-cyanocinnamic acid and other like materials suitable for absorbing energy from a laser. The laser may be a standard nitrogen laser or any laser known in the art. As known in the prior art, mass spectrometry peaks are analyzed by determining ion signals attributes such as peak heights and/or area defined by the peak (relative to baselines). When two peaks are compared, typically a ratio is determined. A peak ratio can be determined from independent sets of reactions from one or more samples for comparison and can be used over time to screen and/or monitor the individual for Type I or Type II diabetes and various blood disorders. The extent of glycation can be analyzed and compared through a variety of calculations that are readily used to those skilled in the art. For example, the extent of glycation can be analyzed by comparing the peak height of a glycated peptide to that of a non-glycated peptide as shown in the formula, $$\% \text{ Glycation} = \frac{\text{Glycated Peptide Intensity}}{(\text{Non-Glycated Peptide Intensity} + \text{Glycated Peptide Intensity})} \times 100 \quad (2)$$

According to another exemplary embodiment, a peptide profile can be analyzed by comparing the peak area of an individual peak to the peak areas of other individual peaks. In other examples, the peak area or height of individual peaks or combination of peaks may be compared to the peak height or area of an individual peak or a combination of peaks in a peptide profile. Accordingly, the exemplary methods of the present disclosure include any combination of calculations performed on one or more peaks within a peptide profile that enable comparisons of one or more peaks to another peak or peaks in the same peptide profile or different peptide profiles.

The exemplary disclosure illustrates certain mass spectrometric peaks observed in blood samples after being modified are indicative of the presence or absence of variants, including but not inclusive of sickle cell anemia, and diabetes. Examples of peak ratios in a peptide profile that can screen for Type I and Type II diabetes that originate from human blood and are analyzed by MALDI MS include but are not limited to, peaks at m/z values from about 3000 for glycated peaks to about 4000 for non-glycated peaks.

Screening and Monitoring for Type I and Type II Diabetes and Blood Disorders

Certain embodiments of the present disclosure relate to the screening and monitoring methods of diabetes and blood disorders. Certain methods of the disclosure are useful for screening, monitoring, evaluating, and controlling the presence, absence or severity of diabetes and blood disorders. The peptide profile may also be used to detect a change in health status. Comparison of an individual peptide profile to a predetermined baseline is useful as a predictor of a change on the health status of an individual. For example, an exemplary diabetes screening method may comprise monitoring a peptide profile over a selected time period to enable assessment of therapy efficacy. For example, the progress of a patient being treated for diabetes could be monitored using the methods described herein to determine if a therapeutic scheme was able to decrease the change in the patient's peptide profile.

While the technology can be applied to measure the extent of glycation of glycopeptides, glycoproteins and glycolipids, it is especially useful in the field of screening, and monitoring where it can be applied to diabetes and blood disorder testing. The exemplary technology relates to a specific, robust, rapid, low cost, automated, direct molecular method for simultaneous quantification of hemoglobin and other blood protein glycation in whole blood by MALDI MS.

Kits

Certain exemplary embodiments of the present disclosure relate to kits comprising elements configured to facilitate certain assay steps. Such kits may relate to the collection, storage, or shipping of biological samples to screen and monitor for Type I and Type II diabetes and blood disorders. Generally, an exemplary kit can include a container, a matrix, matrix solution and/or pre-spotted MALDI targets and one amine reagent. An exemplary kit can also comprise packaging material, instructions, a storage buffer, and/or materials on which the sample can be dried. An exemplary patient kit can include a container, packaging material, instructions, a storage buffer or material on which the sample can be dried. Exemplary kits can also be used to collect the biological samples. Suitable samples are exemplified by blood and the like.

MALDI-MS Techniques and Instrumentation

Those skilled in the art will understand that similar useful results are obtainable with methods adapted for use with mass spectrometry instruments exemplified by MALDI-QQQ (triple quadrupole), MALDI-Q-TOF (quadrupole time-of-flight), MALDI-iontrap-TOF (time-of-flight), MALDI-FTICR-MS (Fourier transform ion cyclotron resonance) and the like, using mass spectrometric techniques exemplified by single reaction monitoring, multiple reaction monitoring and the like.

Example 1

Figure 2:
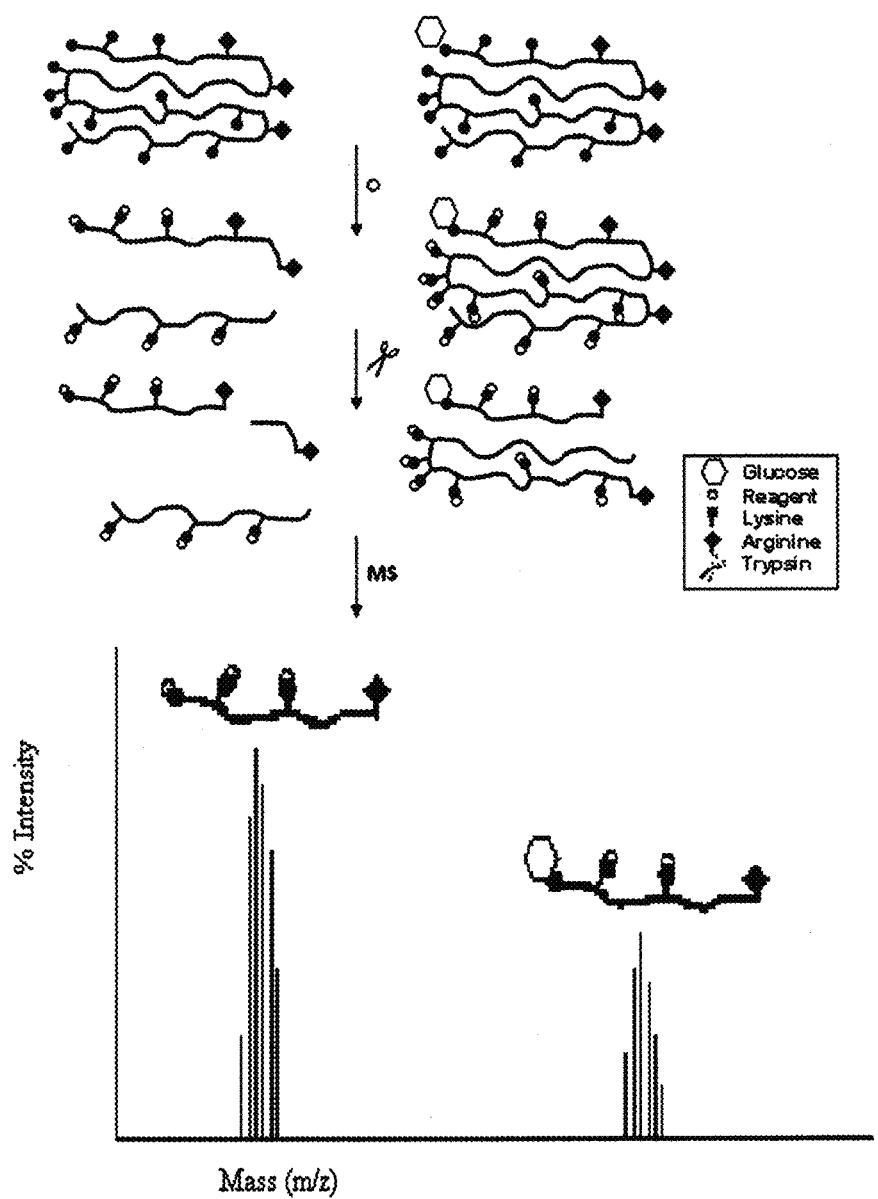
FIG. 2 is a flowchart illustrating an exemplary method of the present disclosure for screening and monitoring for glycated and non-glycated hemoglobin and/or albumin, with an accompanying chart aligned with their mass spectra.

An exemplary method according to the present disclosure shown in FIG. 2 illustrates the steps of modifying proteins in a biological sample with an exemplary amine reagent and then analyzing the modified proteins with mass spectrometry. The first step comprises collecting a blood sample either via a dry blood spot and/or a liquid blood sample. The sample is then modified with an exemplary amine reagent wherein the amines preferentially bind to the alpha amino groups of N-terminals and/or epsilon amino groups of lysine side chains. The next step is application of a blocking reagent followed by digestion with trypsin whereby the proteins are cleaved. The cleaved proteins, now referred to as peptides, are analysed with MALDI MS wherein the ion signals corresponding to the specific pairs of glycated and non-glycated N-terminal peptides are measured. The mass spectrum of a non-glycated peptide is shown on the left side of the chart shown in FIG. 2, and is not indicative of diabetes. The ratio of glycated peptide sample indicative of diabetes is illustrated in the mass spectra in the right hand side of the chart in FIG. 2. The chart in FIG. 2 shows that the mass of the glucose modified peptide is different than the non-glucose modified peptide.

Example 2

Blood is drawn from a subject and is diluted or placed directly on a paper sheet exemplified by tissue paper. Blood from a subject is obtained by a finger prick and a drop is collected on a small piece of paper. The blood sample is then dried on the paper piece and is subsequently stored at room temperature. Suitable dry blood spot samples can be as small as and less than 1 µl. Biological fluids that are analyzed according to this method of the disclosure preferably include whole blood.

Example 3

For the purpose of the examples discussed herein, an exemplary amine reagent was prepared and incubated with whole blood as follows. About 0.2 µl of 0.3M solution of pyridinecarboxylic acid N-hydroxysuccinimide ester in dimethylsulfoxide and 0.2 td 1M triethylcarbonate buffer, pH 8.0 was added to 10 µl of whole blood diluted 1:100 with distilled water. The reaction mixture was incubated at room temperature (25° C.) for 30 minutes. 1 µl of 1M ammonium bicarbonate was added and mixture was further incubated for 30 min at room temperature.

Amine reagents for the modification of amino groups having the general formula R1—R2, wherein R1 is a reactive group specific for modification of primary amino groups, and R2 is a modifying group which is conjugated to the amino groups through the reactive group as a result of the reaction.

Suitable, exemplary R1 groups include among others, N-hydroxysuccinimidyl ester; N-hydroxysulfosuccinimidyl ester; isothiocyanate; pentafluorophenyl ester; sulfotetrafluorophenyl ester; sulfonyl chloride; p-nitrophenyl; and aldehyde.

R2 groups are selected for the specific carbohydrate to be measured and can be any group which, following conjugation will produce mass increment differing from the mass of the carbohydrate of interest. R2 groups preferably bear a partial or full positive charge. In the case of pyridinecarboxylic acid N-hydroxysuccinimide (PCAS), R2 differs from 105 Daltons, as this is the mass increment of PCAS.

Suitable, exemplary R2 groups include among others, pyridinyl; piperidinyl; N-alkylpiperidinyl; piperazinyl; N-alkylpiperazinyl; imidazolyl; N-alkylimidazolyl; dialkylamine; and trialkylamine.

0.5 µl of 1 mg/ml trypsin solution in 0.1% acetic acid was added to the mixture and mixture was incubated overnight at room temperature. 0.1 µl of the reaction mixture was spotted onto a MALDI plate and allowed to dry. The spot was overlaid with 0.3 µl of 5 mg/ml α-cyanocinnamic acid matrix solution in 0.1% trifluoroacetic acid 50% acetonitrile. The dried spot was analyzed by MALDI MS. Following the modification reaction, blocking of excessive reagent, trypsin digestions and MALDI MS, the following N-terminal peptides were obtained, with the small captions signifying the modification of N-terminal or lysine residues:

dAHkSEVAHR (SEQ ID NO: 7) N-terminal peptide for albumin;

vLSPADkTNVkAAWGkVGAHAGEYGAEALER (SEQ ID NO: 7) N-terminal peptide for α-chain of hemoglobin, and, vHLTPEEkSAVTALWGkVNVDEVGGEALGR (SEQ ID NO: 9) N-terminal peptides for β-chain of hemoglobin.

Example 4

Figure 3:
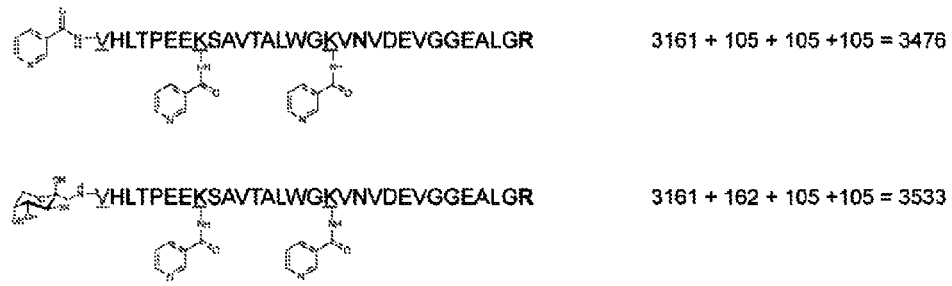
FIG. 3 is a schematic illustrating amine reagent modification of the amino acid sequence of free (top: SEQ ID NO: 9) or glycated (bottoms: SEQ ID NO: 10) β-chain hemoglobin N-terminal and/or lysine side chains with pyridinecarboxylic acid N-hydroxysuccinimide (PCAS)

An exemplary example of the present disclosure relates to the exemplary amine modification method of the present disclosure. Glucose can be non-enzymatically covalently bound to proteins including hemoglobin. The levels of glycated hemoglobin are used as a diagnostic parameter and can screen and/or monitor blood disorders. HbAlc refers to hemoglobin that is glycated at the β-chain N-terminus. An amine reagent modifies the free N-terminal and/or lysine side chain amine groups. FIG. 3 shows the free N-terminal and lysine side chains that have been modified with an amine reagent to produce a weight of 3533 Daltons for the glycated β-hemoglobin peptide with lysine modifications and 3476 Daltons for the β-hemoglobin peptide that is modified at the N-terminal and the lysine side chains. Those skilled in these arts will understand how to configure suitable amine reagents for producing glycated and non-glycated moieties that are separated by at least 10 Daltons by MALDI MS.

Example 5

Figure 4:
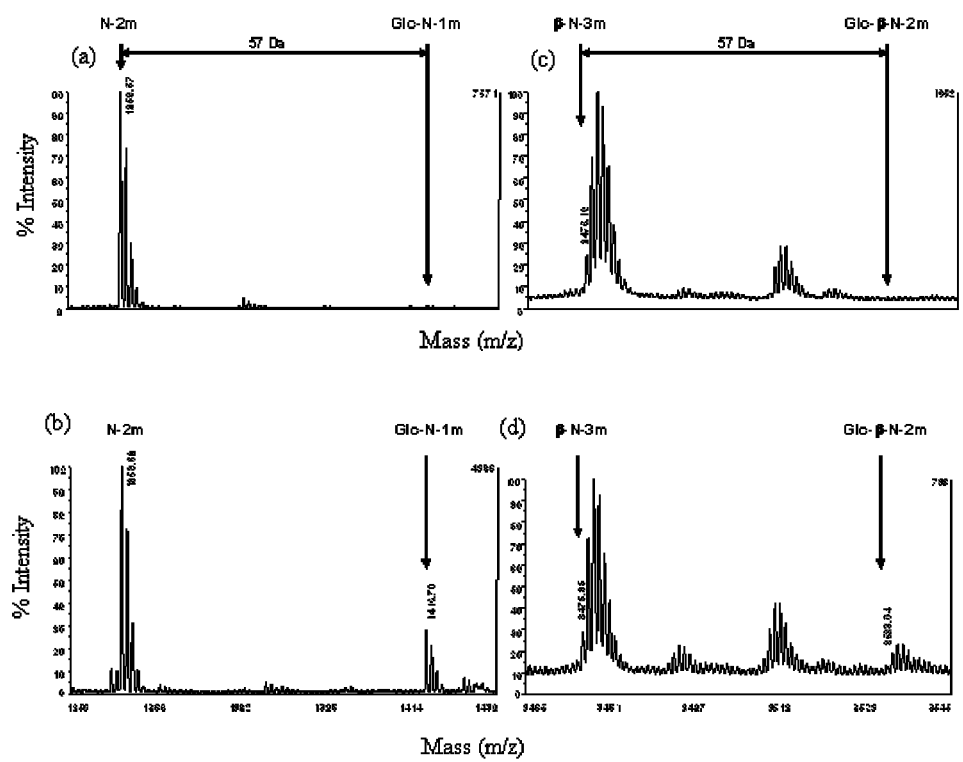
FIG. 4(a) is a chart illustrating an exemplary mass spectrum of in vitro, non-glycated peaks of human serum albumin in phosphate buffered saline, 4(b) is a chart illustrating an exemplary mass spectrum of in vitro, glycated peaks of human serum albumin in phosphate buffered saline, 4(c) is a chart illustrating an exemplary mass spectrum of in vitro, non-glycated peaks of blood in phosphate buffered saline, and 4(d) is a chart illustrating an exemplary mass spectrum of in vitro, glycated peaks of blood in phosphate buffered saline.

An exemplary method for screening and/or monitoring an individual for Type I and Type II diabetes and various blood disorders relates to detecting glycated peptides using MALDI MS. The peptide profiles in FIG. 4 were extremely reproducible and the results relate to the use of the present disclosure as a screening and monitoring method for Type I and Type II diabetes and blood disorders. 20 μl of 3 mg/ml solutions of purified human serum albumin in PBS (FIG. 4(a) without glucose and FIG. 4(b) with glucose) and 1:200 diluted using $H_2O$ of blood in PBS (FIG. 4(c) without glucose and FIG. 4(d) with glucose) with and without 0.5M glucose were heated at 100° C. 10 minutes in water bath. After cooling on ice, the samples were modified with NHS-pyridinecarboxylic acid for 30 minutes at 25° C. after which, excess reagent was blocked with 0.1M ammonium bicarbonate for 30 minutes at 25° C. Samples were digested overnight at 25° C. with 1 μg of trypsin and then measured by MALDI MS. MALDI MS showed in vitro glycation of the hemoglobin and albumin proteins resulting in appearance of the peaks corresponding to the glycated forms of the proteins (FIG. 4(b) and FIG. 4(d)). The glycated peaks corresponding to masses of 1416.70 m/z for human serum albumin and 3533.04 m/z for blood illustrated peptides with mass of 57 Dalton higher than mass of the peaks corresponding to the non-glycated form of the peptides. Peaks are well resolved and the intensities ratio is easily quantifiable. There are no interfering peaks in the mass range of glycated form of the N-terminal hemoglobin peptides for trypsin digest of blood sample, FIG. 4(d).

Example 6

Figure 5:
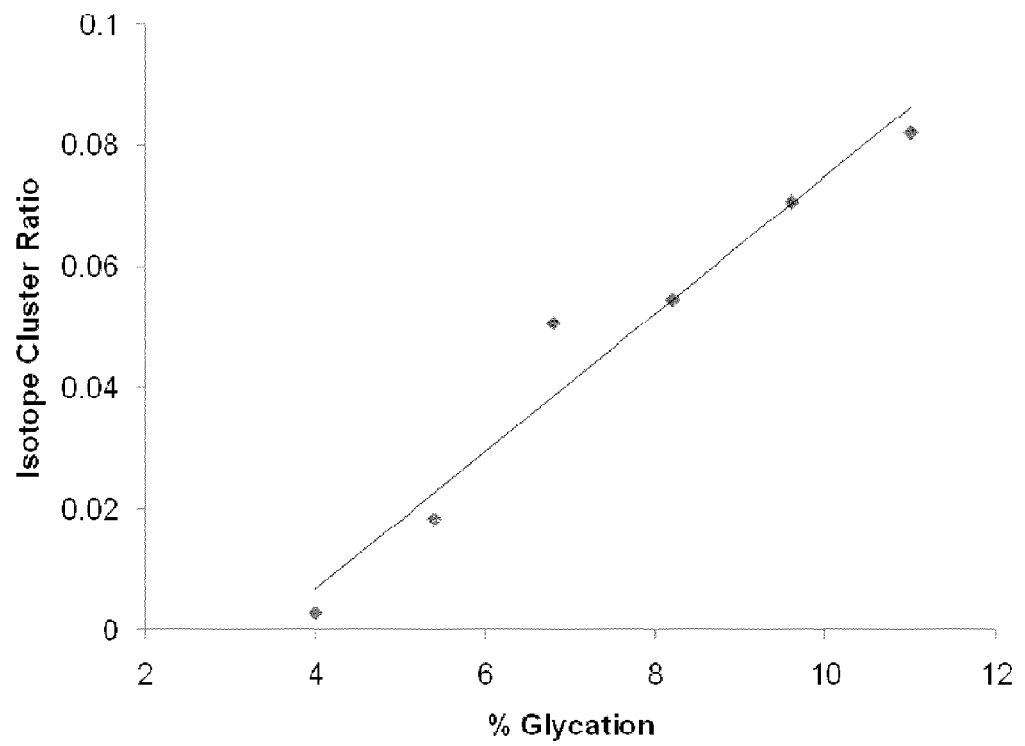
FIG. 5 is a chart illustrating the standard curve using liquid whole blood samples.

An exemplary example of the present disclosure relates to a method to calibrate a standard curve that can be used to analyze unknown samples. Six liquid standard samples, were used to formulate the standard calibration curve illustrated in FIG. 5. The calibration curve has known 4% and 11% glycated samples. The known 4% and 11% glycated samples are mixed to produce the standard calibration samples. The intensities of the non-glycated and glycated peptides were measures and the ratio was determined according to formula (3).

$$\text{Peptide Ratio} = \frac{Ig}{(Ig + In)} \qquad (3)$$

where Ig and In are intensities or cluster peak areas of the glycated and non-glycated peaks respectively.

Example 7

Figure 6:
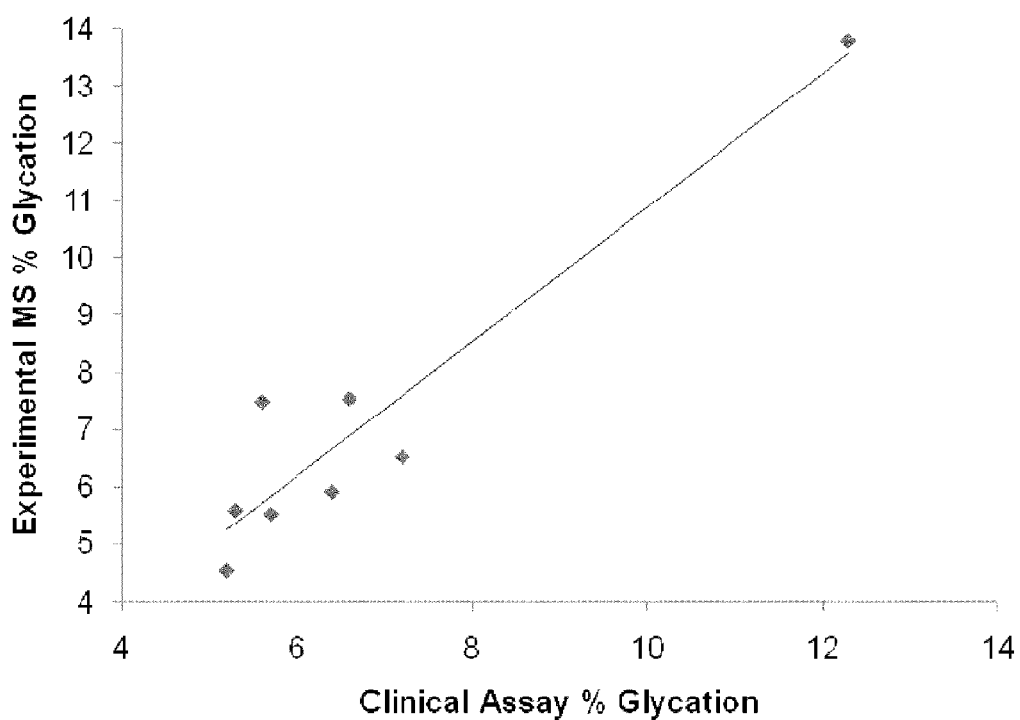
FIG. 6 is a chart comparing % glycation results of an exemplary method of the present disclosure with % glycation results of a prior art assay.

An exemplary example of the present disclosure relates to the correlation between the % glycation determined by a prior art assay and the % glycation of the hemoglobin determined by the exemplary MADLI MS assay as illustrated in FIG. 6. The prior art assay is a immune assay which treats the sampled blood with antibodies against glycated hemoglobin and measures the amount of % glycated hemoglobin through changes in optical absorbance. During the MALDI MS assay the liquid and/or dried blood samples are treated with an amine reagent, blocking reagent and trypsin digest and then analyzed using MADLI MS to detect glycation of hemoglo-bin. Measurements of HbAlc in the 4-6% range are considered normal, less than 7% is a well-controlled diabetic, 7-8% is an average diabetic and greater than 8% is a poorly controlled diabetic. FIG. 6 illustrates a linear curve with a line equation being y=1.1713x−0.8276, with R2=0.8976. The R squared indicates how accurate the regression line is. The closer R squared is to 1, the more accurate the regression line is to sample data.

Example 8

Figure 7:
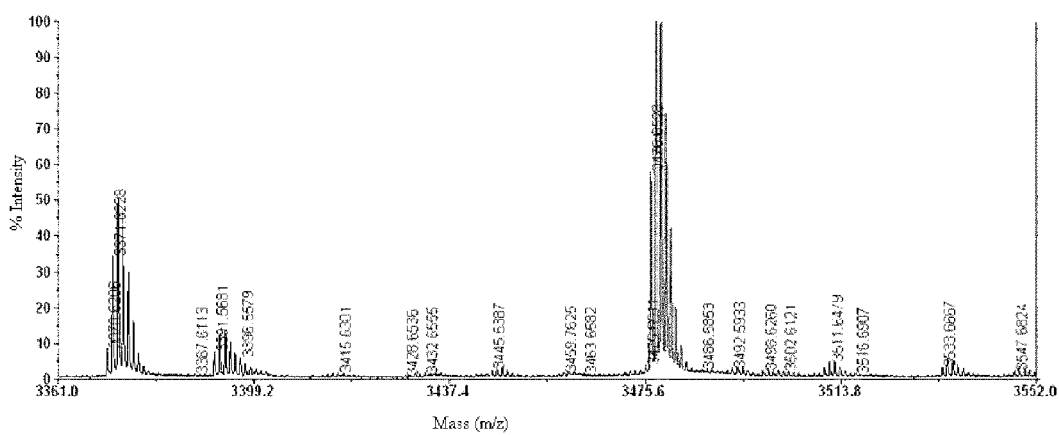
FIG. 7 is a mass spectrum of a blood sample produced with an exemplary method of the present disclosure to screen and monitor for non-glycated and glycated peaks representative of Type I and Type II diabetes.

Peptide peaks were identified from the observed m/z values and the known masses of the N-terminal β-chain of hemoglobin using the exemplary method described in this disclosure to screen and/or monitor for diabetes and blood disorders. FIG. 7 illustrates that the individual in question has non-glycated HbAlc peaks at 3476 Daltons and glycated HbAlc peaks at 3533 Daltons from which ratio of intensities can be calculated using formula (4).

$$\text{Peptide Ratio} = \frac{Hg}{(Hg + Hn)} \qquad (4)$$

where Hg and Hn are intensities or cluster peak heights of the glycated and non-glycated peaks respectively.

Example 9

Figure 8:
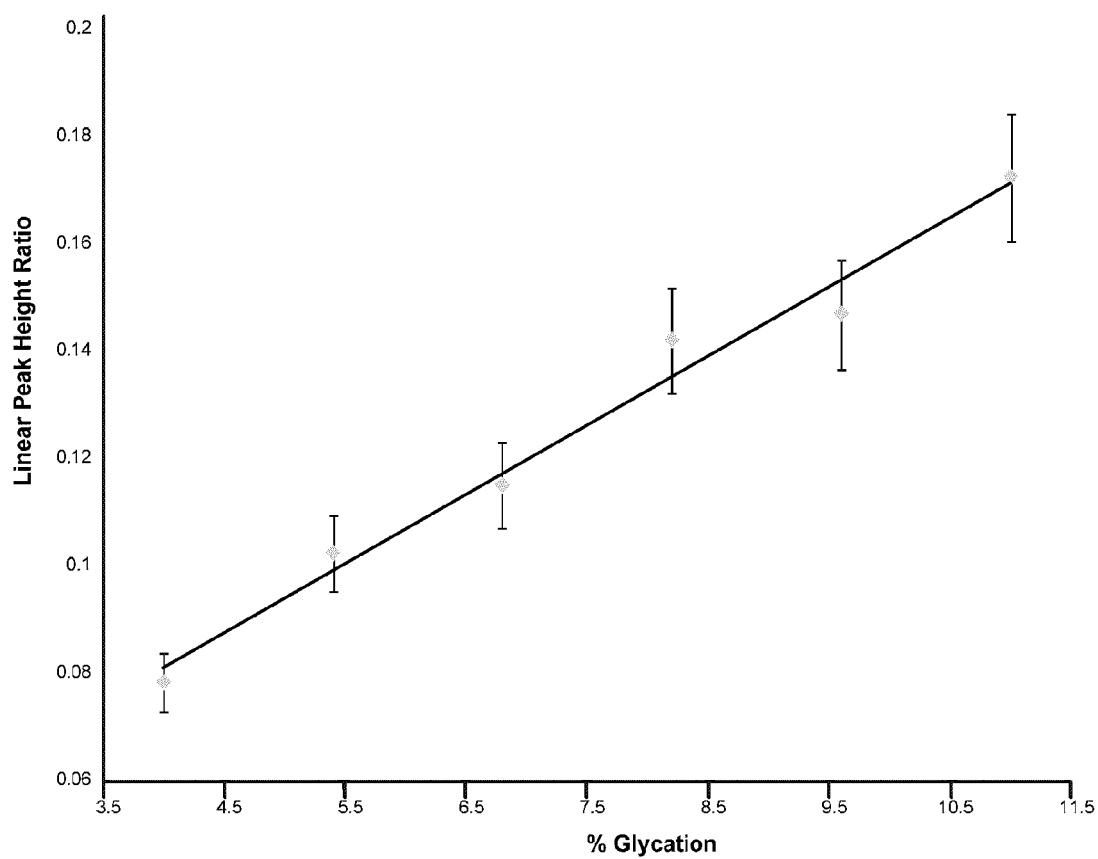
FIG. 8 is a chart illustrating the standard curve using whole blood dried blood spot samples.
Figure 9:
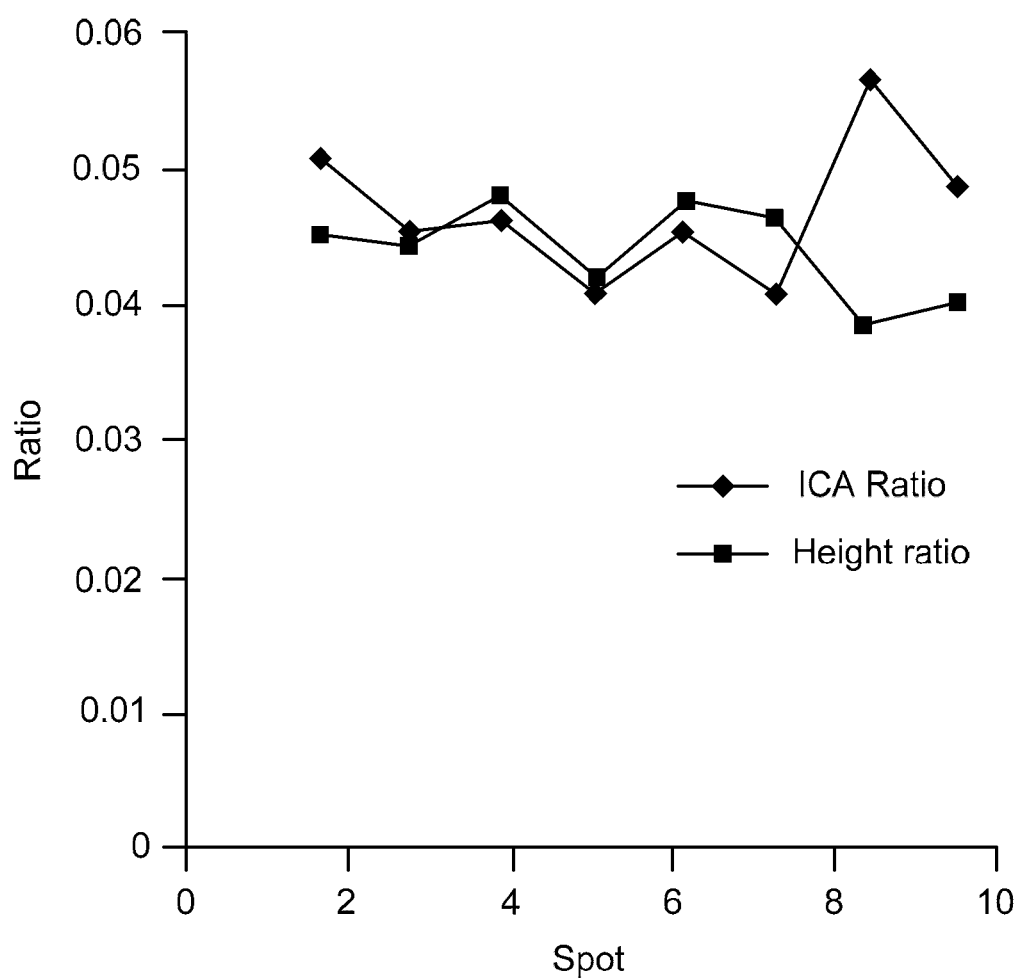
FIG. 9 is a chart comparing isotopic cluster area ratio with height ratio results of an exemplary method of the present disclosure.

An exemplary example of the present disclosure relates to the method to calibrate a standard curve that can be used to analyze unknown samples. Six liquid blood standard samples, were used to formulate the standard calibration curve illustrated in FIG. 8. The calibration curve has known 4% and 11% glycated samples. The known 4% and 11% glycated samples are mixed to produce the standard calibration samples and then dried on tissue paper. The intensities of the dried blood spots of the non-glycated and glycated peptides were measures using MALDI MS and the ratio was determined according to formula (4).

Example 10

An exemplary example of the present disclosure relates to the estimation of the reproducibility of the assay for the Isotopic Cluster Area Ratios or the Height Ratios determined by the exemplary method using dried blood spots. The same sample of standard mixture containing 5.4% HbAlc was equally applied to eight spots on a MALDI plate and each spot was analysed using an exemplary method of the present disclosure. From this type of analysis, statistical parameters of the measurements can be estimated.

Example 11

Figure 10:
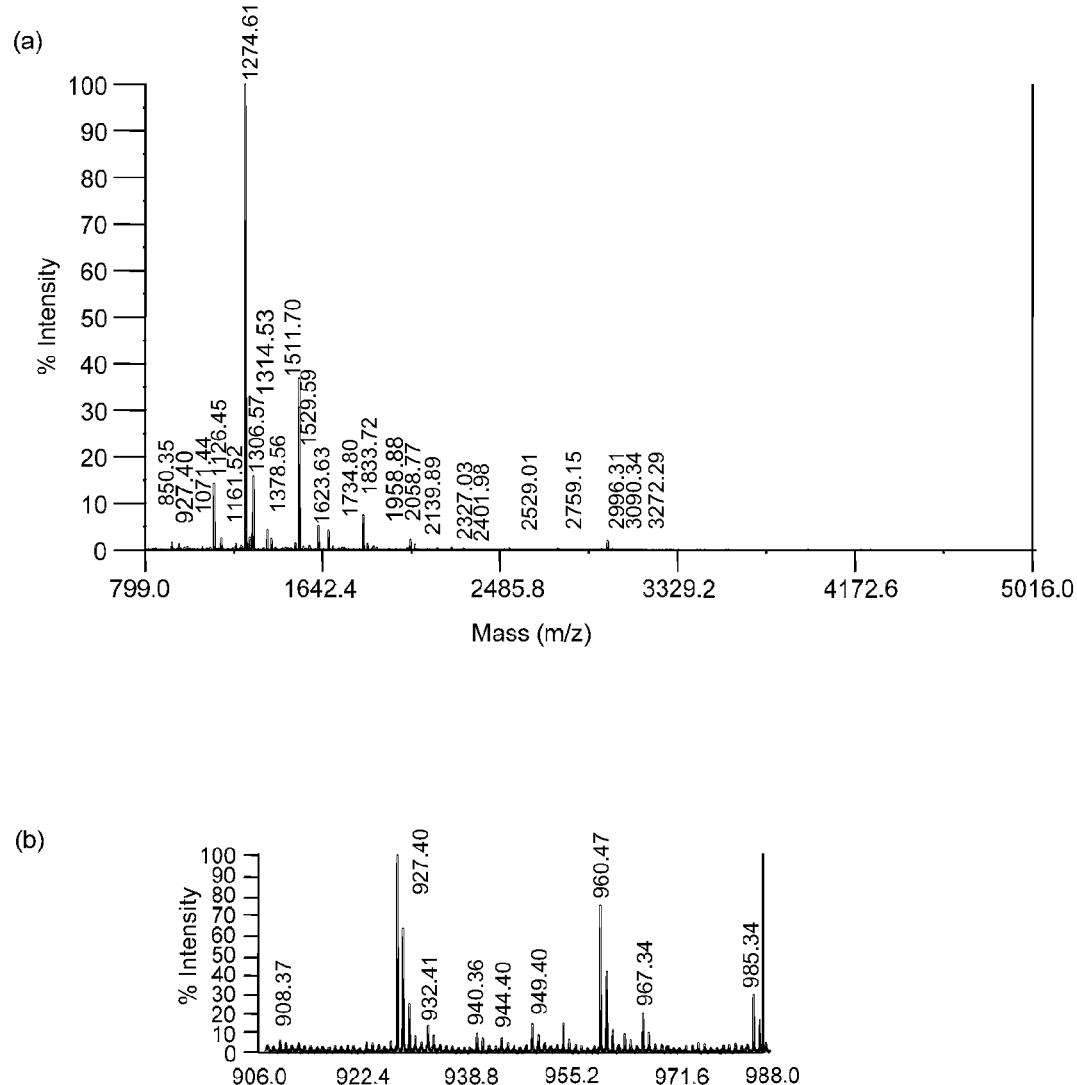
FIG. 10(a) is a mass spectrum of a whole blood sample produced with mutations in both S genes of hemoglobin with no modification reagent, 10(b) is a mass spectrum of the 906 m/z to 988 m/z region.

Peptide peaks of a whole dried blood sample were analyzed for a known sample that had mutations in both hemoglobin S genes. The whole blood sample was diluted in distilled water (1:100) and not modified using the exemplary disclosure. The mutant peptide that was not identified using MALDI MS has the amino acid sequence VHLTPVEK (SEQ ID NO: 6), while it is known in the prior art that the normal peptide sequence is VHLTPEEK (SEQ ID NO: 3). FIGS. 10 (a) and (b) illustrates that no peptide is present at 922.54 m/z thus indicating that the mutated peptide is not detected using the standard MALDI procedure known in the prior art.

Example 12

Peptide peaks of a whole dried blood sample were analyzed for a known sample that had mutations in both hemoglobin S genes. The whole blood sample was diluted in distilled water (1:100) and modified using the amine reagent, blocking agent and trypsin digest as explained in the exemplary method of the present disclosure. The peptide that was identified using the exemplary method has the amino acid sequence (SEQ ID NO: 1)
VHLTPVEKSAVTALWGKVNVDEVGGEALGR.

Figure 11:
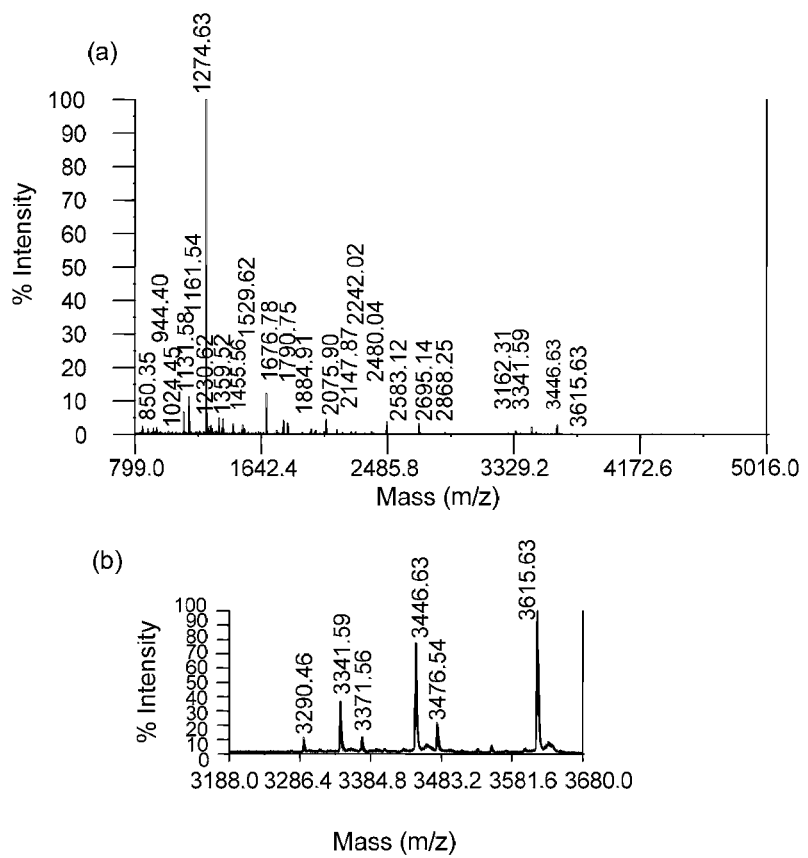
FIG. 11(a) is a mass spectrum of a whole blood sample produced with mutations in both S genes of hemoglobin with an exemplary method of the present disclosure to screen and monitor for variants, 11(b) is a mass spectrum of the 3188 m/z to 3680 m/z region.

The PCAS amine reagent bound to the lysine and N-terminus, thus illustrating that a peptide at 3446.63 m/z is present, as shown in FIGS. 11 (a) and (b).

Example 13

Figure 12:
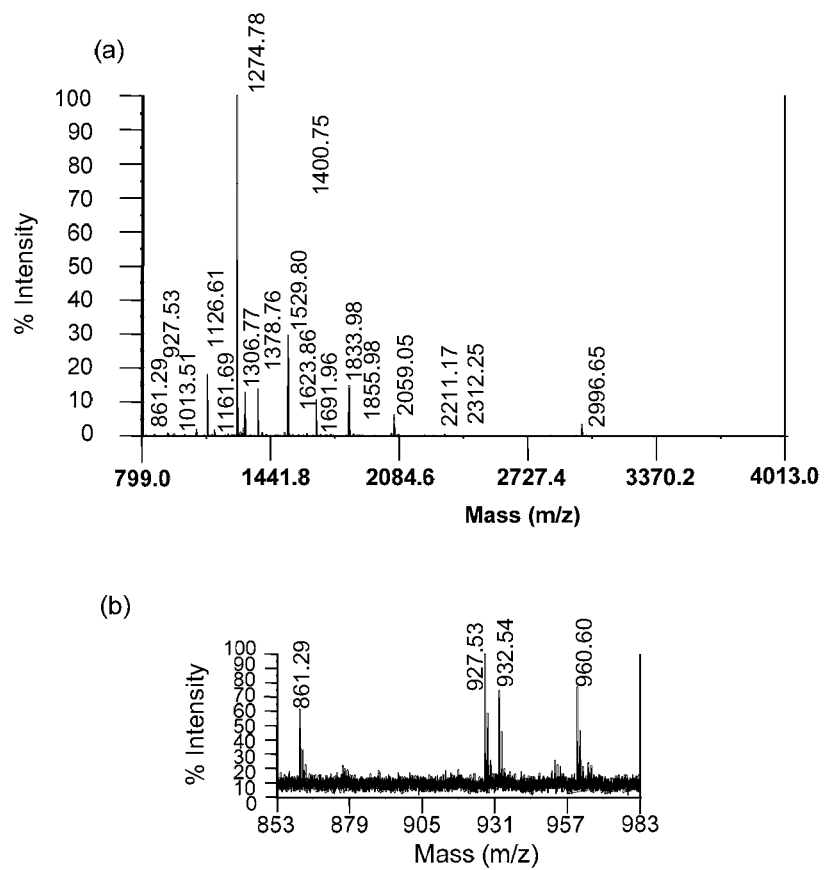
FIG. 12(a) is a mass spectrum of a whole blood sample produced with a mutation in one C gene of hemoglobin with no modification reagent, 12(b) is a mass spectrum of the 853 m/z to 983 m/z region.

Peptide peaks of a whole dried blood sample were analyzed for a known sample that had a normal gene and a mutation in the hemoglobin C gene. The whole blood sample was diluted in distilled water (1:100) and not modified using the exemplary method. The peptide that was not identified using MALDI MS has the amino acid sequence VHLTPKEK (SEQ ID NO: 2), while it is known in the prior art that the normal peptide sequence is VHLTPEEK (SEQ ID NO: 3). FIGS. 12 (a) and (b) illustrates that no peptide is present at 951.56 m/z indicating that the mutated peptide is not detected using the standard MALDI procedure known in the prior art.

Example 14

Figure 13:
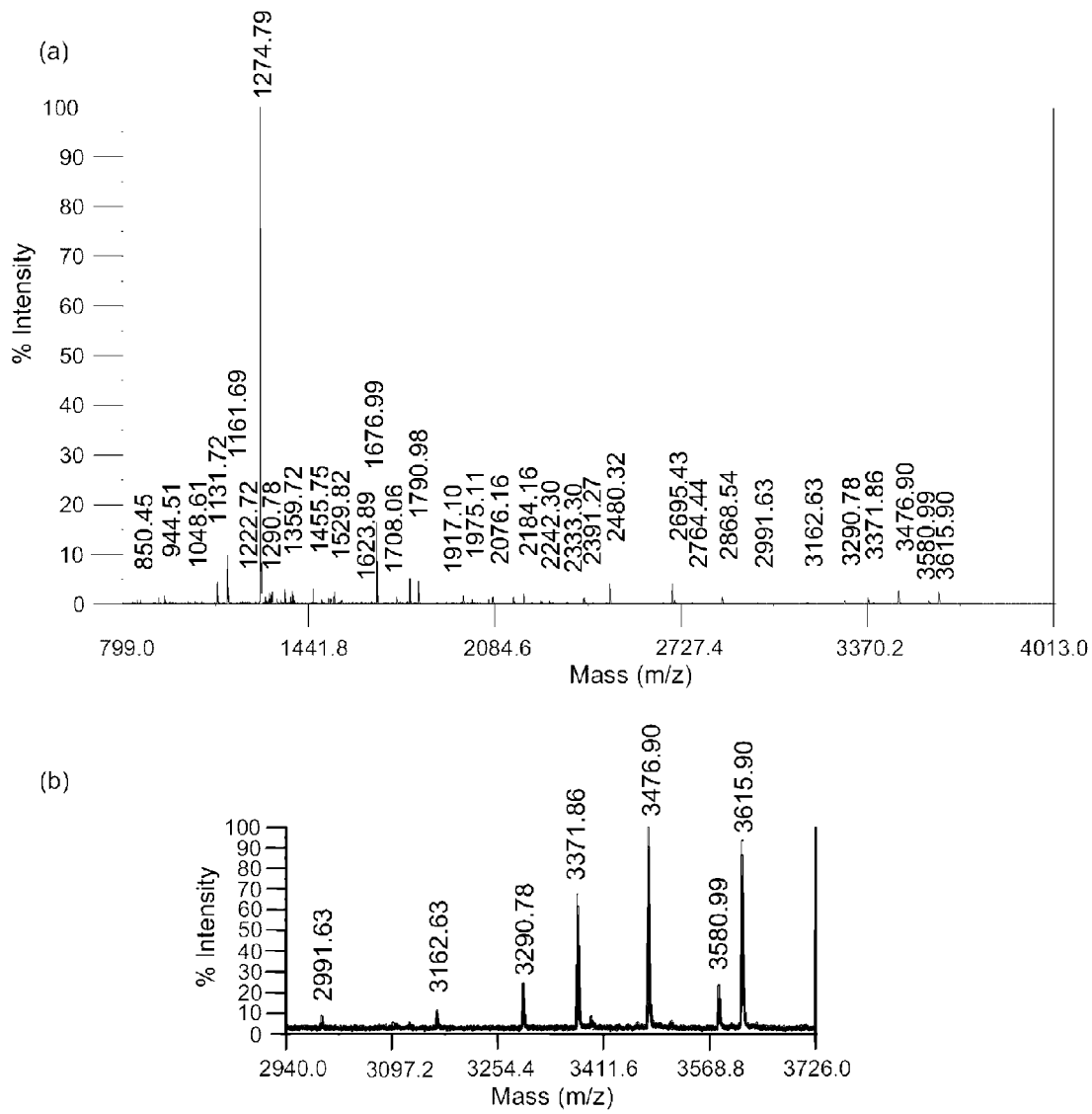
FIG. 13(a) is a mass spectrum of a whole blood sample produced with a mutation in one C gene of hemoglobin with an exemplary method of the present disclosure to screen and monitor for variants, 13(b) is a mass spectrum of the 2940 m/z to 3726 m/z region.

Peptide peaks of a whole dried blood sample were analyzed for a known sample that had a normal gene and a mutation in the hemoglobin C gene. The whole blood sample was diluted in distilled water (1:100) and modified using the amine reagent, blocking agent and trypsin digest as explained in the exemplary method of the present disclosure. The normal peptide and the mutated peptide were identified using the exemplary method and has the amino acid sequence VHLTPEEKSAVTALWGKVNVDEVGGEALGR (SEQ ID NO: 4) and VHLTPKEKSAVTALWGKVNVDEVGGEALGR (SEQ ID NO: 5) respectively. The PCAS amine reagent bound to the lysine and N-terminus, illustrating the normal heterozygous peptide at 3476.90 m/z and the mutated modified peptide at 3580.99 m/z, as shown in FIGS. 13 (a) and (b).

Example 15

Figure 14:
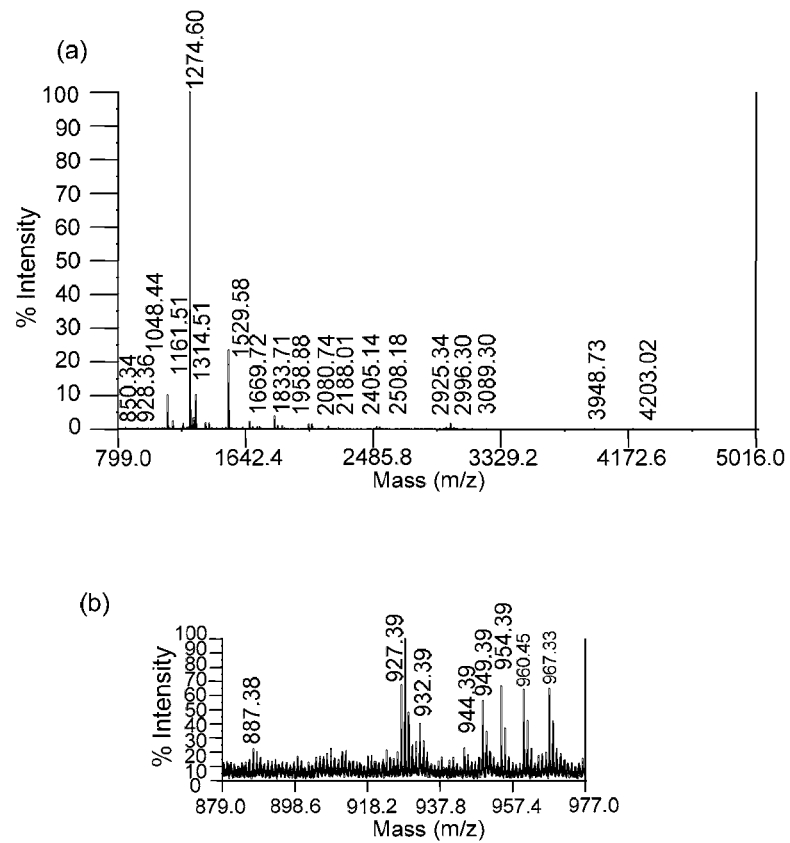
FIG. 14(a) is a mass spectrum of a whole blood double mutant gene sample produced with no modification reagent as in the exemplary method of the present disclosure to screen and monitor for variants, 14(b) is a mass spectrum of the 879 m/z to 977 m/z region.

Peptide peaks of a whole dried blood sample were analyzed for a known sample that had a double mutant, one mutation in the S gene and one mutation in the C gene of hemoglobin. The whole blood sample was diluted in distilled water (1:100) and not modified using the exemplary method of the present disclosure. The peptides that were not identified using MALDI MS had the amino acid sequence VHLTPVEK (SEQ ID NO: 6) and VHLTPKEK (SEQ ID NO: 2), while it is known in the prior art that the normal peptide sequence is VHLTPEEK (SEQ ID NO: 3). FIGS. 14 (a) and (b) illustrates that no peptides are present at 922.54 m/z and 951.56 m/z indicating the mutated S and C peptides respectively, are not detected using the standard MALDI procedure known in the prior art.

Example 16

Figure 15:
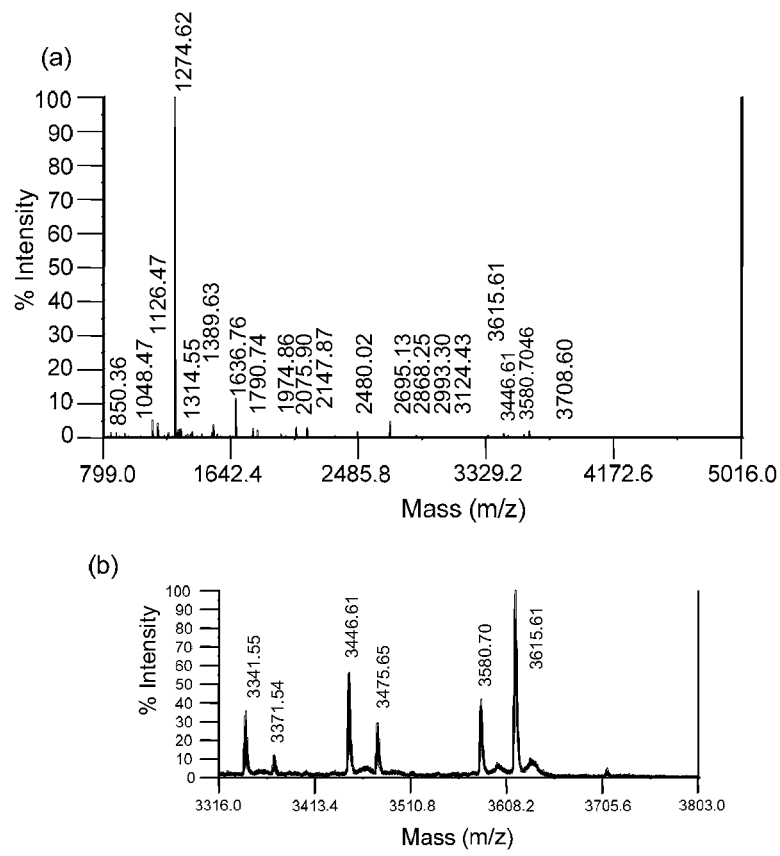
FIG. 15(a) is a mass spectrum of a whole blood double mutant gene sample produced with an exemplary method of the present disclosure to screen and monitor for variants, 15(b) is a mass spectrum of the 3316 m/z to 3803 m/z region.

Peptide peaks of a whole dried blood sample were analyzed for a known sample that had a double mutantation, one mutation in the S gene and one mutation in the C gene of hemoglobin. The whole blood sample was diluted in distilled water (1:100) and modified using the amine reagent, blocking agent and trypsin digest as explained in the exemplary method of the present disclosure. The S and C mutant peptides were identified using the exemplary method and have the amino acid sequences VHLTPVEKSAVTALWGKVNVDEVGGEALGR (SEQ ID NO: 1) and VHLTPKEKSAVTALWGKVNVDEVGGEALGR (SEQ ID NO: 5) respectively. The PCAS amine reagent bound to the lysine and N-terminus, illustrating the mutant S peptide at 3446.61 m/z and the mutant C peptide at 3580.70 m/z, as shown in FIGS. 15 (a) and (b).

---

What is claimed is:

1. A method for detecting a blood disorder in a subject, comprising:
    contacting a blood sample obtained from a subject with an amine reactive reagent, thereby modifying said blood sample;
    blocking any of the amine reactive reagent in the modified blood sample with a blocking reagent selected therefor;
    subsequently digesting the modified blood sample with a trypsin composition, thereby producing a digested blood sample comprising a first plurality of glycated N-terminal peptides and a second plurality of non-glycated N-terminal peptides;
    analyzing said digested blood sample with MALDI MS to detect therein and separate therefrom the first plurality of glycated N-terminal peptides and the second plurality of non-glycated N-terminal peptides;
    comparing and correlating said first plurality of glycated N-terminal peptides and the second plurality of non-glycated N-terminal peptides with at least one selected reference data set; and
    determining therefrom said comparison and correlation the presence or absence of the blood disorder.

2. The method according to claim 1, wherein the first plurality of N-terminal peptides comprise at least one of albumin, α-hemoglobin, and β-hemoglobin.

3. The method according to claim 1, wherein said blood sample is a dried blood sample.

4. The method according to claim 3, wherein said dried blood sample is storable.

5. The method according to claim 1, where said blood sample is a liquid blood sample.

6. The method according to claim 5, wherein said liquid blood sample is storable.

7. The method according to claim 1, wherein a detection of elevated glycated β-hemoglobin in comparison to the reference data set is an indicator of a diabetes condition.

8. The method according to claim 1, wherein said blood sample is a whole blood sample.

9. The method according to claim 1, wherein said amine reactive reagent modifies one of a plurality of N-terminals and a plurality of lysine side chains of protein components in the blood sample.

10. The method according to claim 1, wherein said blood sample is a fractionated blood sample.

11. The method according to claim 1, wherein the amine reactive reagent comprises a general formula of R1—R2 wherein R1 is a reactive group specific for modification of primary amino groups.

12. The method according to claim 11, wherein the R1 group is selected from the group consisting of an N-hydroxysuccinimidyl ester, N-hydroxysulfosuccinimidyl ester, isothiocyanate, pentafluorophenyl ester, sulfotetrafluorophenyl ester, sulfonyl chloride, p-nitrophenyl, aldehyde, and combinations thereof.

13. The method according to claim 11, wherein the R2 group is selected from the group consisting of a pyridinyl, piperidinyl, N-alkylpiperidinyl, piperazinyl, N-alkylpiperazinyl, imidazolyl, N-alkylimidazolyl, dialkylamine, trialkylamine, and combinations thereof.

14. The method of claim 1, wherein comparing and correlating comprises quantifying the first plurality of glycated N-terminal peptides and quantifying the second plurality of non-glycated N-terminal peptides.

15. The method of claim 1, wherein comparing and correlating comprises determining a percent of glycation of the N-terminal peptides.

16. The method of claim 1, wherein the blood disorder is sickle cell, hemoglobin C, hemoglobin S-C, hemoglobin E, thalassemia or analbuminaemia.

17. The method of claim 1, wherein the blood disorder is associated with type I or type II diabetes or a mutated hemoglobin.

* * * * *